United States Patent [19]

Haga et al.

[11] 4,327,089
[45] Apr. 27, 1982

[54] O-(N-ALKOXY-PYRIDINECARBOXIMID-OYL) PHOSPHATES, PROCESS FOR PRODUCING THE SAME, AND INSECTICIDAL OR ACARIDICAL COMPOSITIONS CONTAINING THE SAME

[75] Inventors: Takahiro Haga, Kusatsu; Tadaaki Toki; Toru Koyanagi, both of Moriyama; Osamu Imai, Kusatsu, all of Japan

[73] Assignee: Ishihara Sangyo Kaisha Ltd., Osaka, Japan

[21] Appl. No.: 215,777

[22] Filed: Dec. 12, 1980

[30] Foreign Application Priority Data

Dec. 12, 1979 [JP] Japan .................. 54-160268

[51] Int. Cl.³ .............. A01N 57/16; G07F 9/58
[52] U.S. Cl. ..................... 424/200; 546/22; 546/24; 546/25
[58] Field of Search ............... 546/22, 24, 25; 424/200; 260/944

[56] References Cited

U.S. PATENT DOCUMENTS 4,054,650 10/1977 Lorenz et al. .................. 260/944
4,076,808 2/1978 Lorenz et al. .................. 424/211

Primary Examiner—Alan L. Rotman
Attorney, Agent, or Firm—Sughrue, Mion, Zinn, Macpeak and Seas

[57] ABSTRACT

A novel O-(N-alkoxy-pyridinecarboximidoyl)-phosphate represented by the following formula:

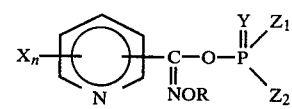

wherein X is a halogen atom, a lower alkyl group, a lower acyloxy group, a trifluoromethyl group or a nitro group; Y is an oxygen atom or a sulfur atom; R is a lower alkyl group; n is an integer of 0 to 3; and $Z_1$ and $Z_2$ are each a lower alkoxy group, a lower alkylthio group, a phenyl group which may be substituted by a lower alkyl group, a phenoxy group, a haloalkoxy group or a lower alkylamino group, useful as an active ingredient of insecticides or acaricides.

19 Claims, No Drawings

O-(N-ALKOXY-PYRIDINECARBOXIMIDOYL) PHOSPHATES, PROCESS FOR PRODUCING THE SAME, AND INSECTICIDAL OR ACARIDICAL COMPOSITIONS CONTAINING THE SAME

FIELD OF THE INVENTION

This invention relates to a novel O-(N-alkoxypyridinecarboximidoyl)phosphate, a process for producing the same, and an insecticide or acaricide containing the same.

BACKGROUND OF THE INVENTION

An insecticide or acaricide containing an O-(N-alkoxy-carboximidoyl)phosphate has heretofore been known; for example, U.S. Pat. No. 4,054,650 discloses that O,O-diethyl-O-(N-methoxy-2-nitrobenzimidoyl)thionophosphate has an insecticidal or acaricidal activity and U.S. Pat. No. 4,076,808, O,S-dialkyl-O-(N-methoxy-benzimidoyl)dithiophosphate.

It was, however, not known that an O-(N-alkoxypyridinecarboximidoyl)phosphate has such insecticidal or acaricidal activity.

SUMMARY OF THE INVENTION

It has now been found according to this invention that those compounds represented by the following formula (I) have an insecticidal or acaricidal activity.

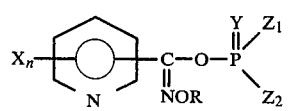

wherein X is a halogen atom, a lower alkyl group, a lower acyloxy group, a trifluoromethyl group or a nitro group; Y is an oxygen atom or a sulfur atom; R is a lower alkyl group; n is an integer of 0 to 3; and $Z_1$ and $Z_2$ are each a lower alkoxy group, a lower alkylthio group, a phenyl group which may be substituted by a lower alkyl group, a phenoxy group, a haloalkoxy group or a lower alkylamino group.

In particular, the compounds according to this invention, in which the benzene nucleus of the compounds disclosed in U.S. Pat. No. 4,054,650 described above and the like is replaced by a pyridine nucleus, are improved in systemic activity to plant, insecticidal activity or acaricidal activity against insects or acarids including those having a resistivity against the conventional chemicals, as compared to those disclosed in U.S. Pat. No. 4,054,650, thus they exhibiting excellent properties.

DETAILED DESCRIPTION OF THE INVENTION

In the definition for the formula (I) above, the halogen atom includes fluorine, chlorine, bromine and iodine; the "alkyl group" in the lower alkyl group, lower alkoxy group, lower alkylthio group and lower alkylamino group means an alkyl group having 1 to 4 carbon atoms, such as methyl, ethyl, n-propyl, isopropyl, n-butyl, sec-butyl, tert-butyl, isobutyl, etc.; the lower acyloxy group includes acetyloxy, propionyloxy, etc.; and the haloalkoxy group includes trifluoroethoxy, etc.

Of the compounds represented by the formula (I), those represented by the following formula (III) are preferred.

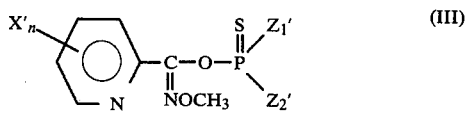

wherein X' is a halogen atom, a lower alkyl group, a trifluoromethyl group or a nitro group; $Z_1'$ and $Z_2'$ are each a lower alkoxy group, a lower alkylthio group or a phenyl group; and n is the same as defined in the formula (I) above.

More preferred are those represented by the formula (IV) below:

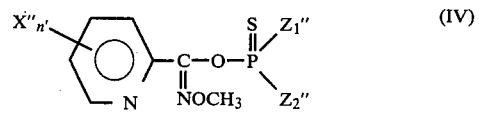

wherein X" is a halogen atom or a trifluoromethyl group; n' is an integer of 0 to 2; and $Z_1"$ and $Z_2"$ are each a lower alkoxy group or a phenyl group.

In the above formulae (I), (III) and (IV), when the pyridine nucleus has a substituent represented by $X_n$, $X'_n$ or $X"_{n'}$ wherein n or n' is 2 or higher, the substituent may be the same or different.

The compound represented by the formula (I) of this invention is usually prepared by reacting an N-alkoxypyridinecarboximidic acid represented by the formula (A):

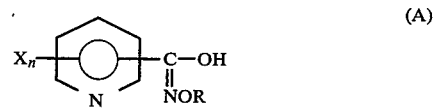

wherein X, R and n are the same as described above, and a known phosphoric halide represented by the formula (B):

wherein Hal is a halogen atom, and Y, $Z_1$ and $Z_2$ are the same as described above,
in the presence of an alkaline material.

Examples of the alkaline materials which can be used include sodium hydroxide, potassium hydroxide, sodium carbonate, potassium carbonate, potassium methylate, etc.

The above reaction is preferably carried out in an inert organic solvent. Examples of the inert organic solvents which can be used are nitriles such as acetonitrile, propionitrile, etc., ethers such as dioxane, diethyl ether, etc., ketones such as acetone, methyl ethyl ketone, methyl isobutyl ketone, etc., and aprotic solvents such as tetrahydrofuran.

The reaction temperature is 0° to 150° C., preferably 20° to 90° C., and the reaction time is 1 is 30 hours, preferably 2 to 10 hours. The reaction is usually carried out at atmospheric pressure.

The N-alkoxy-pyridinecarboximidic acid represented by the formula (A) can easily be prepared by, for example, (1) a method in which pyridine-hydroxamic acid is reacted with an alkylating agent, such as an alkyl halide, a dialkylsulfuric acid, etc., and (2) a method in which a picolinic acid derivative, such as a halide or ester of picolinic acid, is reacted with an O-alkoxyamine.

SYNTHESIS EXAMPLE 1

Synthesis of O,O-Diethyl-O-(N-methoxy-pyridine-2-carboximidoyl)thionophosphate (A) Preparation of N-Methoxy-pyridine-2-carboximidic Acid 6.8 g (0.08 mol) of an O-methylhydroxylamine hydrochloric acid salt was dissolved in 20 ml of water, and 22.4 g (0.16 mole) of potassium carbonate dissolved in 20 ml of water was dropwise added thereto at 0° C. 14.2 g (0.08 mol) of a picolinyl chloride hydrochloric acid salt was further added thereto, and the resulting solution was stirred at 0° to 10° C. for 4 hours. The reaction product thus obtained was extracted with methylene chloride several times. The organic phase was dried over anhydrous sodium sulfate to obtain 8.4 g of N-methoxypyridine-2-carboximidic acid.

(B) Preparation of the Desired Product 8.4 g (0.055 mol) of N-methoxy-pyridine-2-carboximidic acid was dissolved in 40 ml of acetonitrile, and 9 g (0.065 mol) of a powder of potassium carbonate was added thereto. The mixture was heated to 50° C. with stirring, and 10.4 g (0.055 mol) of O,O-diethylthionophosphoric acid diester chloride was dropwise added thereto. The resulting mixture was then further reacted at 50° C. for 24 hours with stirring. The reaction product was allowed to cool and poured into a suitable amount of water. An oily phase was extracted with methylene chloride. The extracted phase was washed successively with a saturated sodium chloride aqueous solution, a 2 N-sodium hydroxide solution and water, and then dried over anhydrous sodium sulfate. After the drying, the solvent was distilled off under reduced pressure, and the residue was purified by silica gel column chromatography using an n-hexane-ethyl acetate mixed solvent as an eluent, to obtain 8.2 g of the desired product ($n_d^{32.8}$ 1.5199).

SYNTHESIS EXAMPLE 2

Synthesis of O-Ethyl-O-(N-methoxy-pyridine-2-carboximidoyl)-N-sec-butyl Phosphoramidethioate 3 g (0.02 mol) of N-methoxy-pyridine-2-carboximidic acid was dissolved in 40 ml of acetonitrile, and 3.2 g (0.02 mol) of potassium carbonate was added thereto. The mixture was heated to 50° C. with stirring, and after dropwise addition of 4.3 g (0.02 mol) of O-ethyl-N-sec-butyl thionophosphoric acid amide ester chloride, the reaction was conducted at 50° C. for 24 hours while stirring. The reaction product was allowed to cool and poured into a suitable amount of water. An oily phase was extracted with methylene chloride. The extracted phase was washed successively with a saturated sodium chloride aqueous solution, a 2 N-sodium hydroxide solution and water, and then dried over anhydrous sodium sulfate. After the drying, the solvent was distilled off under reduced pressure, and the residue was purified by silica gel column chromatography using an n-hexane-ethyl acetate mixed solvent as an eluent to obtain 4.2 g of the desired product ($n_D^{20.0}$ 1.5410).

SYNTHESIS EXAMPLE 3

Synthesis of O-Ethyl-O-(N-ethoxy-pyridine-2-carboximidoyl)-phenyl Phosphonothionate (A) Preparation of N-Ethoxy-pyridine-2-carboximidic Acid 7 g (0.05 mol) of pyridine-2-hydroxamic acid and 1.4 g (0.05 mol) of sodium hydride were dissolved in 100 ml of ethanol, and 8 g (0.05 mol) of ethyl iodide was gradually dropwise added thereto with stirring. After the dropwise addition, the reaction solution was stirred for 2 hours under reflux condition. After completion of the reaction, the ethanol was distilled off under reduced pressure. To the residue were added suitable amounts of methylene chloride and water, whereby the desired product was extracted with the methylene chloride. The extract was washed with a saturated sodium chloride aqueous solution, and dried over anhydrous sodium sulfate. After the drying, the solvent was distilled off under reduced pressure to obtain 8.2 g of the desired product.

(B) Preparation of the Desired Product 2 g (0.012 mol) of N-ethoxy-pyridine-2-carboximidic acid was dissolved in 40 ml of acetonitrile, and 2 g (0.014 mol) of a powder of potassium carbonate was added thereto. The mixture was heated to 50° C. while stirring, and after dropwise addition of 2.7 g (0.012 mol) of O-ethylphenylthionophosphoric acid chloride, the reaction was conducted at 50° C. for 8 hours while stirring. The reaction product was allowed to cool, poured into a suitable amount of water, and an oily phase was extracted with methylene chloride. The extracted phase was washed successively with a saturated sodium chloride aqueous solution, a 2 N-sodium hydroxide aqueous solution and water, and dried over anhydrous sodium sulfate. After the drying, the solvent was distilled off under reduced pressure, and the residue was purified by silica gel column chromatography using an n-hexane-ethyl acetate mixed solvent as an eluent to obtain 3.1 g of the desired product ($n_D^{23.4}$ 1.5710).

Examples of the compounds of the formula (I) of this invention are shown in Table 1.

TABLE 1

$$X_n-\underset{N}{\underset{\|}{\bigcirc}}-\underset{NOR}{\overset{\|}{C}}-O-\overset{Y}{\underset{Z_2}{\overset{\|}{P}}}{\diagup}^{Z_1}$$

| Compound No. | Pyridyl Moiety | Y | R | $Z_1$ | $Z_2$ | Physical Properties |
|---|---|---|---|---|---|---|
| 1 | ⟨◯⟩-<br>N | S | $CH_3$ | $-OCH_3$ | $-OCH_3$ | $n_D^{22.5}$ 1.5489 |
| 2 |  | S | " | $-OC_2H_5$ | $-OC_2H_5$ | $n_D^{32.8}$ 1.5199 |
| 3 | " | O | " | $-OC_2H_5$ | $-SC_3H_7-n$ | $n_D^{20.5}$ 1.5310 |

TABLE 1-continued $$X_n-\text{(pyridyl)}-\underset{\underset{NOR}{\parallel}}{C}-O-\underset{\underset{Z_2}{|}}{\overset{\overset{Y}{\parallel}}{P}}-Z_1$$

| Compound No. | Pyridyl Moiety | Y | R | $Z_1$ | $Z_2$ | Physical Properties |
|---|---|---|---|---|---|---|
| 4 | " | O | " | —OC$_3$H$_7$—n | —OC$_3$H$_7$—n | $n_D^{23.0}$1.4715 |
| 5 | " | O | " | —OC$_2$H$_5$ |  | $n_D^{19.8}$1.5515 |
| 6 | " | S | " | —OC$_2$H$_5$ | " | $n_D^{18.3}$1.5947 |
| 7 | " | O | " | —O— | —O— | $n_D^{15.5}$1.5980 |
| 8 |  | S | CH$_3$ | —OC$_2$H$_5$ | —OC$_2$H$_5$ | $n_D^{22.5}$1.5345 |
| 9 |  | " | " | —OC$_2$H$_5$ | —OC$_2$H$_5$ | $n_D^{20.3}$1.5315 |
| 10 |  | " | " | —OC$_2$H$_5$ | —OC$_2$H$_5$ | $n_D^{23.0}$1.5340 |
| 11 |  | " | " | —OC$_2$H$_5$ | —OC$_2$H$_5$ | $n_D^{18.3}$1.5490 |
| 12 |  | " | " | —OC$_2$H$_5$ | —OC$_2$H$_5$ | $n_D^{22.0}$1.5065 |
| 13 |  | " | " | —OC$_2$H$_5$ | —OC$_2$H$_5$ | $n_D^{22.5}$1.5321 |
| 14 |  | S | CH$_3$ | —OC$_2$H$_5$ | —OC$_2$H$_5$ | $n_D^{15.5}$1.5329 |
| 15 |  | " | " | " | " | $n_D^{15.5}$1.5898 |
| 16 |  | " | " | " | " | $n_D^{16.0}$1.5080 |
| 17 |  | " | " | " | " | $n_D^{16.0}$1.5054 |
| 18 |  | " | " | " | " | $n_D^{20.0}$1.5210 |
| 19 |  | " | " | " | NHCHC$_2$H$_5$<br>$\|$<br>CH$_3$ | $n_D^{20.0}$1.5410 |
| 20 |  | S | CH$_3$ | —OC$_2$H$_5$ |  | $n_D^{17.8}$1.5479 |
| 21 |  | " | " | " | —OC$_2$H$_5$ | $n_D^{15.0}$1.5876 |
| 22 |  | " | " | —OCH$_3$ |  | $n_D^{15.5}$1.6180 |
| 23 | " | " | " | —OC$_3$H$_7$—n | " | $n_D^{15.5}$1.6019 |
| 24 | " | " | " | —SC$_2$H$_5$ | " | $n_D^{16.8}$1.6300 |
| 25 |  | " | " | —OC$_2$H$_5$ | " | $n_D^{19.0}$1.5880 |

TABLE 1-continued $$X_n-\underset{N}{\bigcirc}-\underset{\|}{\overset{}{C}}-O-\overset{\overset{Y}{\|}}{\underset{\|}{P}}\overset{Z_1}{\underset{Z_2}{}}$$
$$\phantom{X_n-\bigcirc-C-O-P}NOR$$

| Compound No. | Pyridyl Moiety | Y | R | $Z_1$ | $Z_2$ | Physical Properties |
|---|---|---|---|---|---|---|
| 26 | Cl–⟨N⟩– | " | " | –OCH$_3$ | " | $n_D^{15.1}$ 1.6074 |
| 27 | ⟨N⟩– | S | C$_2$H$_5$ | –OC$_2$H$_5$ | " | $n_D^{23.4}$ 1.5710 |
| 28 | ⟨N⟩– | " | " | –OC$_2$H$_5$ | $n_D^{23.4}$ 1.5175 | |
| 29 | " | " | C$_3$H$_7$–n | " | –⟨◯⟩ | $n_D^{27.5}$ 1.5666 |
| 30 | " | " | C$_3$H$_7$–i | " | " | $n_D^{25.5}$ 1.5650 |
| 31 | " | " | CH$_3$ | " | –⟨◯⟩–CH$_3$ | $n_D^{14.4}$ 1.5998 |
| 32 | " | " | " | –OCH$_2$CF$_3$ | –⟨◯⟩ | $n_D^{17.6}$ 1.5548 |

TEST EXAMPLE 1

Diamondback Moth (*Plutella xylostella*)-Control Test 20 parts by weight of an active ingredient, 60 parts by weight of xylene and 20 parts by weight of a mixture of a polyoxyethylene phenyl phenol derivative, a polyoxyethylene sorbitan alkylate and an alkylaryl sulfonate were uniformly mixed to prepare an emulsifiable concentrate which was then diluted with water to provide an emulsion having a concentration of the active ingredient of 200 ppm.

A section of cabbage leaf was immersed in the emulsion for about 10 seconds, taken out therefrom and dried in air. A wetted filter paper was placed on a Petri dish (diameter: 9 cm), and the section was placed thereon. Some 2nd to 3rd instar larvae of diamondback moth were released on the lamina and allowed to stand in a covered thermostat with illumination of 28° C. Two days after the release of larvae, the alive and dead of the larvae were evaluated. The percent mortality was calculated by the following equation:

$$\text{Percent Mortality} = \frac{\text{Number of Dead Larvae}}{\text{Number of Released Larvae}} \times 100 \, (\%)$$

The results obtained are shown in Table 2-1.

TABLE 2-1

| Compound No. | Percent Mortality (%) |
|---|---|
| 1 | 100 |
| 5 | 100 |
| 10 | 100 |
| 11 | 100 |
| 12 | 100 |
| 13 | 100 |
| 17 | 100 |
| 21 | 100 |
| 22 | 100 |
| 23 | 100 |
| 24 | 50 |
| 25 | 90 |
| 26 | 100 |
| 27 | 100 |
| 28 | 100 |

TABLE 2-1-continued

| Compound No. | Percent Mortality (%) |
|---|---|
| 31 | 90 |
| 32 | 100 |

Comparison in activity between the compounds of this invention and O,O-diethyl-O-(N-methoxy-2-nitrobenzimidoyl)thionophosphate disclosed in U.S. Pat. No. 4,054,650 (hereinafter referred to as "comparison compound") was made in the same manner as in Test Example 1 except that the concentration of the active ingredient in each emulsion was reduced. The results obtained are shown in Table 2—2.

TABLE 2-2

| Compound No. | Percent Mortality (%) Concentration of Active Ingredient | | |
|---|---|---|---|
| | 100 ppm | 25 ppm | 6.25 ppm |
| 1 | 100 | 100 | 100 |
| 2 | 100 | 80 | 90 |
| 6 | 80 | 70 | 70 |
| Comparison Compound | 0 | 0 | 0 |

TEST EXAMPLE 2

Housefly (*Musca domestica*)-Control Test

A powdery feed (produced by Oriental Yeast Industry Co., Ltd.) as a culture medium for larvae of housefly, bran and the same emulsion as prepared in Test Example 1 which had been adjusted to a predetermined concentration of the active ingredient were mixed in a weight ratio of 1:1:2, and the mixture was placed in a cup (diameter: 7 cm, height: 4 cm). Some 2nd to 3rd instar larvae of housefly were released into the cup, and the cup was then covered with gauze. Twelve days after the release of larvae, the alive and dead were evaluated. The percent mortality was measured in the same manner as in Test Example 1. The results obtained are shown in Table 3-1.

TABLE 3-1

| Compound No. | Percent Mortality (%) Concentration of Active Ingredient | | |
|---|---|---|---|
| | 40 ppm | 10 ppm | 2.5 ppm |
| 2 | 100 | 100 | 100 |
| 11 | 100 | 100 | 100 |
| 12 | 100 | 100 | 100 |

Comparison in activity between the compounds of this invention and the comparison compound was made in the same manner as in Test Example 2 except that the concentration of active ingredient in the emulsion was reduced. The results obtained are shown in Table 3–2.

TABLE 3-2

| Compound No. | Percent Mortality (at 0.6 ppm) (%) |
|---|---|
| 1 | 90 |
| 2 | 100 |
| Comparison Compound | 40 |

TEST EXAMPLE 3

Azuki Bean Weevil (*Callosobruchus chinensis*)-Control Test

The same emulsifiable concentrate as prepared in Test Example 1 was adjusted to provide an emulsion having a predetermined concentration of the active ingredient. 1 ml of the emulsion was uniformly attached to the inside bottom surface of a 9 cm Petri dish and dried in air to provide a Petri dish with the predetermined amount of the active ingredient attached in the form of a film on the inner surface thereof. After releasing 15 adult azuki bean weevils thereinto, the dish was covered and placed for 24 hours in a thermostat maintained at 25° C. Thereafter, the alive and dead were evaluated to thereby measure the percent mortality in the same manner as in Test Example 1. The results obtained are shown in Table 4–1.

TABLE 4-1

| Compound No. | Percent Mortality (%) Amount of Active Ingredient | | |
|---|---|---|---|
| | 100 μg/dish | 50 μg/dish | 25 μg/dish |
| 1 | 100 | 100 | 100 |
| 2 | 100 | 100 | 100 |
| 3 | 100 | 100 | 100 |
| 9 | 100 | 100 | 100 |
| 10 | 100 | 100 | 100 |
| 11 | 100 | 100 | 100 |
| 12 | 100 | 100 | 100 |
| 13 | 100 | 100 | 100 |
| 14 | 100 | 100 | 100 |
| 16 | 100 | 100 | 100 |
| 17 | 100 | 100 | 100 |
| 18 | 100 | 100 | 100 |
| 20 | 100 | 100 | 100 |
| 21 | 100 | 100 | 100 |
| 22 | 100 | 100 | 100 |
| 26 | 100 | 100 | 100 |
| 27 | 100 | 100 | 100 |
| 28 | 100 | 100 | 100 |

Comparison in activity between the compounds of this invention and the comparison compound was made in the same manner as in Test Example 3 except that the concentration of the active ingredient in the emulsion was reduced. The results obtained are shown in Table 4–2.

TABLE 4-2

| Compound No. | Percent Mortality (at 3.125 μg/dish) (%) |
|---|---|
| 1 | 90 |
| 2 | 100 |
| 6 | 60 |
| 11 | 100 |
| 17 | 100 |
| Comparison Compound | 0 |

TEST EXAMPLE 4

Green Rice Leafhopper (*Nephotettix cincticeps*)- and Smaller Brown Planthopper (*Delphacodes striatella*) -Control Test A wettable powder as prepared in Formulation Example 3 set forth hereinbelow was adjusted to a concentration of active ingredient of 100 ppm to prepare a solution. Only the root part of rice plant seedling was immersed in the solution for 48 hours. After completely washing the root part with water, the stem part was covered with defatted cotton and placed in a test tube. Some 3–4 instar larvae of green rice leafhopper and smaller brown planthopper were released into the test tube, and the test tube was then covered with gauze. After 48 hours, the alive and dead of the larvae were evaluated to thereby measure the percent mortality in the same manner as in Test Example 1. The results obtained are shown in Table 5–1.

TABLE 5-1

| Compound No. | Percent Mortality | |
|---|---|---|
| | Green Rice Leafhopper (%) | Smaller Brown Planthopper (%) |
| 1 | 100 | 100 |
| 2 | 100 | 100 |
| 4 | 100 | 100 |
| 6 | 100 | 100 |
| 11 | 100 | 100 |
| 12 | 100 | 100 |
| 18 | 100 | — |
| 19 | 100 | — |
| 20 | 100 | — |
| 21 | 100 | — |
| 22 | 100 | — |
| 23 | 100 | — |
| 24 | 40 | — |
| 25 | 100 | — |
| 26 | 100 | — |
| 27 | 100 | 100 |
| 28 | 100 | 100 |
| 31 | 100 | — |
| 32 | 100 | — |

Comparison in activity between the compounds of this invention and the comparison compound was made in the same manner as in Test Example 4 except that the concentration of active ingredient in the solution was adjusted to 25 ppm. The results obtained are shown in Table 5–2.

TABLE 5-2

| Compound No. | Percent Mortality | |
|---|---|---|
| | Green Rice Leafhopper (%) | Smaller Brown Planthopper (%) |
| 1 | 60 | 100 |
| 2 | 100 | 100 |
| 6 | — | 100 |

TABLE 5-2-continued

| Compound No. | Percent Mortality | |
|---|---|---|
| | Green Rice Leafhopper (%) | Smaller Brown Planthopper (%) |
| 10 | 60 | 100 |
| 17 | 50 | 100 |
| Comparison Compound | 0 | 50 |

TEST EXAMPLE 5

Carmine Mite (*Tetranychus telarius*) -Control Test

A kidney bean young plant whose leaves were cut leaving one primary leaf was planted in an ice cream cup, inoculated with about 30 larvae and adults of carmine mite, and then immersed for 10 seconds in the emulsion as used in Test Example 1 and adjusted to a concentration of the active ingredient of 200 ppm. After drying in air, the plant was placed in a thermostat with illumination and maintained at 28° C. Three days after, the alive and dead of the larvae and adults were evaluated to thereby measure the percent mortality in the same manner as in Test Example 1. The results obtained are shown in Table 6-1.

TABLE 6-1

| Compound No. | Percent Mortality (%) |
|---|---|
| 1 | 100 |
| 2 | 100 |
| 4 | 100 |
| 6 | 100 |
| 11 | 100 |
| 12 | 100 |
| 18 | 100 |
| 19 | 50 |
| 20 | 100 |
| 21 | 100 |
| 22 | 100 |
| 23 | 100 |
| 24 | 100 |
| 25 | 90 |
| 26 | 100 |
| 31 | 70 |
| 32 | 100 |

Comparison in activity between the compounds of this invention and the comparison compound was made in the same manner as in Test Example 5 except that the concentration of active ingredient in the emulsion was adjusted to 25 ppm. The results obtained are shown in Table 6-2.

TABLE 6-2

| Compound No. | Percent Mortality (%) |
|---|---|
| 1 | 100 |
| 6 | 100 |
| 21 | 90 |
| 22 | 100 |
| 23 | 90 |
| Comparison Compound | 50 |

TEST EXAMPLE 6

Green Peach Aphid (*Myzus persicae*) -Control Test

On an eggplant seedling (about 20 cm high) which was cultivated in a 1/3,500 are pot and on which a number of green peach aphidae were parasitic was sprayed an emulsion prepared by adjusting an emulsifiable concentrate as prepared in Formulation Example 2 set forth hereinbelow to a concentration of the active ingredient of 50 ppm, in an amount of 20 ml per the pot. The eggplant seedling was held in a greenhouse. Three days after, the reduction in the number of green peach aphidae was observed. The results obtained are shown in Table 7.

The survival rate was evaluated on the following scale:
1—Nearly equal to the untreated plot.
2—Fair survival although a reduction is observed.
3—Fair reduction
4—Slight survival
5—No survival

TABLE 7

| Compound No. | Survival Rate |
|---|---|
| 1 | 5 |
| 2 | 5 |
| 4 | 5 |
| 6 | 5 |
| 11 | 5 |
| 12 | 5 |
| 18 | 4 |
| 20 | 4 |
| 21 | 5 |
| 22 | 5 |
| 23 | 4 |
| 24 | 5 |
| 31 | 5 |

O-(-N-alkoxy-pyridinecarboximidoyl)phosphates of the formula (I) are effective against various harmful insects and acarids.

Examples of such harmful insects against which the compounds of this invention are effective are Hemiptera such as aphidae [e.g., cotton aphid (*Aphis gossypii*), cabbage aphid (*Brevicoryne brassicae*), green peach aphid (*Myzus persicae*), etc.], coccidae [e.g., *Lesanium cerni, Saissetis eleas,* California red scale (*Aonidiella aurantii*), *Aspridiotue hederae*, etc.], deltocephalidae [e.g., green rice leafhopper (*Nephotettix cincticeps*), etc.], delphacidae [e.g., smaller brown planthopper (*Delphacodes striatella*), brown planthopper (*Nilaparvata lugens,* etc.]; Lepidoptera such as diamondback moth (*Plutella xylostella,* Heliothis spp., army worm (*Mamestra brassicae*), tobacco cutwarm (*Spodoptera litura*), etc.; Diptera such as housefly (*Musca domestica*), *Culex pipiens pallens,* etc.; Coleoptera such as azuki bean weevil (*Callosobruchus chinensis*), 28-spotted lady beetle (*Epilachna vigintioctopunctata*), etc.; and so on.

Examples of harmful acarids against of which the compounds of this invention are also effective are two-spotted spider mite (*Tetranychus urticae*), citrus red mite (*Panonychus citri*), etc.

The O-(N-alkoxy-pyridinecarboximidoyl)phosphates as described above exhibit an excellent insecticidal activity, particularly against sucking insects, and an excellent acaricidal effect against acarids of Tetranychus which are resistant against various known acaricides.

The insecticidal or acaricidal composition of this invention is usually used in a concentration of active ingredient of 1 to 10,000 ppm, preferably 20 to 2,000 ppm. In the case of aquatic insects, they can be controlled by spraying the composition in the above concentration range and, therefore, the concentration range in water is effective even below the above-specified range.

When the compounds of this invention are used as active ingredients of the insecticidal or acaricidal composition, it is possible to formulate into various forms, such as dust, wettable powder, emulsifiable concentrate, inert emulsion, oil solution, aerosol preparation, etc., with agriculturally effective amounts of agriculturally acceptable adjuvants. The composition can be applied with or without diluting in suitable concentrations.

Suitable examples of the adjuvants which can be used include powdery carriers such as talc, kaolin, bentonite, diatomaceous earth, silicon dioxide, clay and starch, liquid diluents such as water, xylene, toluene, dimethyl sulfoxide, dimethylformamide, acetonitrile, and alcohols, emulsifiers, dispersing agents, spreaders, etc.

A suitable concentration of the active ingredient in the insecticidal or acaricidal composition is usually 5 to 80% by weight for the case of emulsifiable concentrate, 0.5 to 30% by weight for the case of dust and 5 to 60% by weight for the case of wettable powder, respectively.

It is also possible to combine with other agricultural ingredients such as other insecticides, acaricides, plant growth regulators, etc. Sometimes, synergistic effects were found. For example, organophosphoric acid ester compounds, carbamate compounds, dithio (or thiol) carbamate compounds, organochloro compounds, dinitro compounds, organic sulfur or metal compounds, antibiotics, substituted diphenyl ether compounds, urea compounds, triazine compounds, benzoyl urea compounds, pyrethroid compounds and the like can be exemplified. More specifically, benzoyl urea compounds such as N-(2,6-difluorobenzoyl)-N'-(p-chlorophenyl)urea, and pyrethroid compounds such as α-cyano-3-phenoxybenzyl 2-(4-chlorphenyl)isovalerate can be exemplified.

Formulation examples containing the compound of this invention are shown below.

FORMULATION EXAMPLE 1

| | parts by weight |
| --- | --- |
| O,O-Dimethyl-O-(N-methoxy-pyridine-2-carboximidoyl)-thionophosphate | 20 |
| Xylene | 60 |
| Sorpol 2806B (trade name for a mixture of polyoxyethylenephenyl phenol derivatives polyoxyethylene-alkyl aryl ether, polyoxyethylene-sorbitan alkylate and alkyl arylsulfate, produced by Toho Chemical Industry Co., Ltd.) | 20 |

These ingredients were uniformly mixed and dissolved to provide an emulsifiable concentrate.

FORMULATION EXAMPLE 2

| | parts by weight |
| --- | --- |
| O,O-Diethyl-O-(N-methoxy-pyridine-2-carboximidoyl)-thionophosphate | 70 |
| Xylene | 20 |
| Polyoxyethylene Alkylphenyl Ether | 10 |

These ingredients were uniformly mixed and dissolved to provide an emulsifiable concentrate.

FORMULATION EXAMPLE 3

| | parts by weight |
| --- | --- |
| O,O-Di-n-propyl-O-(N-methoxy-pyridine-2-carboximidoyl)-phosphate | 30 |
| Sodium Dodecylsulfate | 2 |
| Sodium Dinaphthylmethanesulfonate | 3 |
| Fine Silicon Dioxide ($SiO_2 \cdot nH_2O$) | 20 |
| Diatomaceous Earth | 45 |

These ingredients were uniformly mixed to provide a wettable powder.

FORMULATION EXAMPLE 4

| | parts by weight |
| --- | --- |
| O,O-Diethyl-O-(N-methoxy-5-trifluoromethylpyridine-2-carboximidoyl)thionophosphate | 5 |
| Talc | 95 |

These ingredients were uniformly pulverized and mixed to provide a dust.

FORMULATION EXAMPLE 5

| | parts by weight |
| --- | --- |
| O,O-Diethyl-O-(N-methoxy-3,5-dichloropyridine-2-carboximidoyl)-thionophosphate | 5 |
| Sodium Ligninsulfonate | 3 |
| Sodium Alkylbenzenesulfonate | 2 |
| Bentonite | 30 |
| Talc | 60 |

These ingredients were mixed with a suitable amount of water necessary for granulation and granulated to provide a granule.

While the invention has been described in detail and with reference to specific embodiments thereof, it will be apparent to one skilled in the art that various changes and modifications can be made therein without departing from the spirit and scope thereof.

What is claimed is:

1. An O-(N-alkoxy-pyridinecarboximidoyl)phosphate represented by the following formula (I):

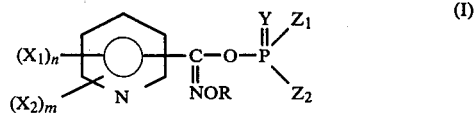

wherein $X_1$ is a halogen atom; $X_2$ is a lower alkyl group having 1 to 2 carbon atoms, an acetyloxy group, a trifluoromethyl group or a nitro group; Y is an oxygen atom or a sulfur atom; R is a lower alkyl group having 1 to 3 carbon atoms; n is an integer of 0 to 3; m is an integer of 0 to 1; and $Z_1$ and $Z_2$ are each a lower alkoxy group having 1 to 3 carbon atoms, a lower alkylthio group having 1 to 3 carbon atoms, a phenyl group which may be substituted with a lower alkyl group having 1 to 4 carbon atoms, a phenoxy group, a haloalkoxy group or a lower alkylamino group having 1 to 4 carbon atoms.

2. A compound of claim 1, which is represented by the following formula (II):

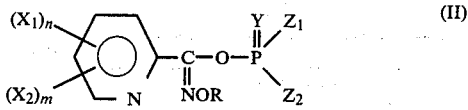

wherein $X_1$, $X_2$, Y, R, n, m, $Z_1$ and $Z_2$ are the same as defined in claim 1.

3. A compound of claim 1, which is represented by the following formula (III):

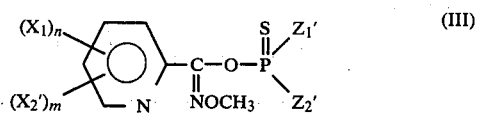

wherein $X_2'$ is a lower alkyl group having 1 to 2 carbon atoms, a trifluoromethyl group or a nitro group; $Z_1'$ and $Z_2'$ are each a lower alkoxy group having 1 to 3 carbon atoms, a lower alkylthio group having 1 to 4 carbon atoms or a phenyl group; and $X_1$, n and m are the same as defined in claim 1.

4. A compound of claim 1, which is represented by the following formula (IV):

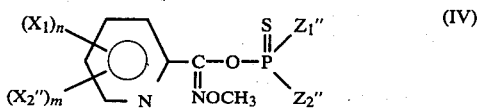

wherein $X_2''$ is a trifluoromethyl group; n' is an integer of 0 to 2; $Z_1''$ and $Z_2''$ are each a lower alkoxy group having 1 to 3 carbon atoms or a phenyl group; and $X_1$ and m are the same as defined in claim 1.

5. A compound of claim 1, wherein the compound is O-ethyl-O-(N-methoxy-pyridine-2-carboximidoyl)phenyl phosphonothionate.

6. A compound of claim 1, wherein the compound is O,O-dimethyl-O-(N-methoxy-pyridine-2-carboximidoyl)-thionophosphate.

7. A compound of claim 1, wherein the compound is O,O-diethyl-O-(N-methoxy-pyridine-2-carboximidoyl)-thionophosphate.

8. A compound of claim 1, wherein the compound is O,O-diethyl-O-(N-methoxy-3,5-dichloropyridine-2-carboximidoyl)thionophosphate.

9. A compound of claim 1, wherein the compound is O,O-diethyl-O-(N-methoxy-3-chloro-5-trifluoromethylpyridine-2-carboximidoyl)thionophosphate.

10. A compound of claim 1, wherein the compound is O-methyl-O-(N-methoxy-pyridine-2-carboximidoyl)-phenyl phosphonothionate.

11. An insecticidal or acaricidal composition comprising an insecticidally or acaricidally effective amount of an O-(N-alkoxy-pyridinecarboximidoyl)phosphate having the formula (I) according to claim 1 as an active ingredient and an agriculturally acceptable adjuvant.

12. An insecticidal or acaricidal composition according to claim 11, which comprises 0.5 to 80 parts by weight of the O-(N-alkoxy-pyridinecarboximidoyl)-phosphate having the formula (I) and 20 to 99.5 parts by weight of the agriculturally acceptable adjuvant.

13. An insecticidal or acaricidal composition according to claim 11, which comprises 0.5 to 80 parts by weight of the O-(N-methoxy-pyridine-2-carboximidoyl)-thionophosphate having the formula (IV) and 20 to 99.5 parts by weight of the agriculturally acceptable adjuvant.

14. An insecticidal or acaricidal composition according to claim 11, wherein the active ingredient is O-ethyl-O-(N-methoxy-pyridine-2-carboximidoyl)phenyl phosphonothionate.

15. An insecticidal or acaricidal composition according to claim 11, wherein the active ingredient is O,O-dimethyl-O-(N-methoxy-pyridine-2-carboximidoyl)-thionophosphate.

16. An insecticidal or acaricidal composition according to claim 11, wherein the active ingredient is O,O-diethyl-O-(N-methoxy-pyridine-2-carboximidoyl)-thionophosphate.

17. An insecticidal or acaricidal composition according to claim 11, wherein the active ingredient is O,O-diethyl-O-(N-methoxy-3,5-dichloropyridine-2-carboximidoyl)thionophosphate.

18. An insecticidal or acaricidal composition according to claim 11, wherein the active ingredient is O,O-diethyl-O-(N-methoxy-3-chloro-5-trifluoromethylpyridine-2-carboximidoyl)thionophosphate.

19. An insecticidal or acaricidal composition according to claim 11, wherein the active ingredient is O-methyl-O-(N-methoxy-pyridine-2-carboximidoyl)phenyl phosphonothionate.

* * * * *